US00PP18086P2

(12) United States Plant Patent
Dörr

(10) Patent No.: US PP18,086 P2
(45) Date of Patent: Sep. 25, 2007

(54) ***BRACTEANTHA* PLANT NAMED 'GOLBRA'**

(50) Latin Name: *Bracteantha bracteata*
Varietal Denomination: Golbra

(75) Inventor: Roland Dörr, Niederösterreich (AT)

(73) Assignee: Ernst Benary Samenzucht GmbH, Hann (DE)

( * ) Notice: Subject to any disclaimer, the term of this patent is extended or adjusted under 35 U.S.C. 154(b) by 0 days.

(21) Appl. No.: 11/415,478

(22) Filed: May 1, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Bracteantha* plant named 'Golbra', characterized by its upright, somewhat outwardly spreading and uniform plant habit; vigorous growth habit; freely flowering habit; daisy-type inflorescences with bright yellow-colored elliptical involucral bracts and orange-colored disc florets; and strong peduncles that hold the inflorescences just above the foliar plane.

1 Drawing Sheet

Botanical designation: *Bracteantha bracteata.*
Cultivar denomination: 'Golbra'.

BACKGROUND OF THE INVENTION

The present invention relates to a new and distinct cultivar of *Bracteantha* plant, botanically known as *Bracteantha bracteata,* and hereinafter referred to by the name 'Golbra'.

The new *Bracteantha* is a product of a planned breeding program conducted by the Inventor in Kittsee, Austria. The objective of the program is to create and develop new *Bracteantha* cultivars with uniformly mounded plant habit, freely flowering habit and attractive inflorescences.

The new *Bracteantha* originated from an open-pollination by the Inventor in 1992 of a non-patented proprietary selection as the female, or seed, parent with an unknown selection of the Bikini-type of *Bracteanthas,* not patented, as the male, or pollen, parent. The new *Bracteantha* was discovered and selected by the Inventor as a single flowering plant within the progeny of the stated open-pollination in a controlled environment in Kittsee, Austria in 2002. The selection of this plant was based on its uniform plant habit, freely flowering habit and attractive inflorescences.

Asexual reproduction of the new *Bracteantha* by terminal cuttings in a controlled environment in Hann. Muenden, Germany since 2002, has shown that the unique features of this new *Bracteantha* are stable and reproduced true to type in successive generations.

SUMMARY OF THE INVENTION

The cultivar Golbra has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Golbra'. These characteristics in combination distinguish 'Golbra' as a new and distinct cultivar of *Bracteantha:*

1. Upright, somewhat outwardly spreading and uniform plant habit.
2. Vigorous growth habit.
3. Freely flowering habit.
4. Daisy-type inflorescences with bright yellow-colored elliptical involucral bracts and orange-colored disc florets.
5. Strong peduncles that hold the inflorescences just above the foliar plane.

In side-by-side comparisons conducted in Lompoc, Calif., plants of the new *Bracteantha* differed from plants of the female parent selection primarily in plant habit as plants of the new *Bracteantha* are more uniform than plants of the female parent selection.

Plants of the new *Bracteantha* can be compared to plants of the *Bracteantha* cultivar Redbragol, disclosed in U.S. Plant Pat. No. 12,988. In side-by-side comparisons conducted in Lompoc, Calif. under natural season conditions, plants of the new *Bracteantha* differed from plants of the cultivar Redbragol in the following characteristics:

1. Plants of the new *Bracteantha* were more upright and not as rounded as plants of the cultivar Redbragol.
2. Plants of the new *Bracteantha* were sturdier than plants of the cultivar Redbragol.
3. Plants of the new *Bracteantha* had brighter colored involucral bracts that plants of the cultivar Redbragol.

BRIEF DESCRIPTION OF THE PHOTOGRAPHS

The accompanying photographs illustrate the overall appearance of the new *Bracteantha.* These photographs show the colors as true as it is reasonably possible to obtain in colored reproductions of this type. Colors in the photographs may differ slightly from the color values cited in the detailed botanical description which accurately describe the colors of the new *Bracteantha.*

The photograph at the bottom of the sheet comprises a side perspective view of a typical flowering plant of 'Golbra' grown in a container.

The photograph at the top of the sheet comprises a close-up view of typical inflorescences of 'Golbra'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lompoc, Calif. during the winter and spring in a polycarbonate-covered greenhouse and under conditions and practices which approximate those generally used in commercial *Bracteantha* production. During the production of the plants, day temperatures ranged from 21° C. to 24° C., night temperatures ranged from 16° C. to 18° C. and light levels ranged from 4,000 foot-candles to 8,000 foot-candles. Measurements and numerical values represent averages for typical flowering plants. Plants were about 13 weeks old when the photographs and description were taken.

Botanical classification: *Bracteantha bracteata* cultivar 'Golbra'.

Parentage:

*Female, or seed, parent.*—Proprietary selection of *Bracteantha bracteata,* not patented.

*Male, or pollen, parent.*—Unknown selection of Bikini-type of *Bracteantha bracteata,* not patented.

Propagation:

*Type.*—Terminal vegetative cuttings.

*Time to initiate roots.*—About one to two weeks.

*Time to produce a rooted cutting.*—About three to four weeks.

*Root description.*—Fine to fibrous; pale brown in color.

*Rooting habit.*—Freely branching.

Plant description:

*Plant form/growth habit.*—Upright, somewhat outwardly spreading and uniform plant habit with dense foliage and inflorescences held above the foliage on strong peduncles. Vigorous growth habit.

*Plant height.*—About 43 cm.

*Plant diameter or spread.*—About 33 cm.

*Lateral branches.*—Quantity per plant: Freely branching habit with lateral branches developing potentially at every node. Length: About 40 cm. Diameter: About 1.2 cm. Internode length: About 1.3 cm. Aspect: Mostly upright. Strength: Strong. Texture: Pubescent. Color: 146B.

*Foliage description.*—Arrangement: Alternate, simple, sessile. Length: About 13.5 cm. Width: About 2.3 cm. Shape: Linear elliptic. Apex: Acute. Base: Attenuate. Margin: Entire. Texture, upper and lower surfaces: Minute pubescence. Venation pattern: Pinnate. Color: Developing foliage, upper surface: 147A. Developing foliage, lower surface: 146B. Fully expanded foliage, upper surface: 147A; venation, 147C. Fully expanded foliage, lower surface: 147B; venation, 146C. Petiole: Length: About 1 cm. Diameter: About 9 mm. Color, upper surface: 146B. Color, lower surface: 146C.

Inflorescence description:

*Appearance.*—Daisy-type inflorescence form with elongated oblong-shaped ray florets. Involucral bracts and disc florets developing acropetally on a capitulum. Inflorescences circular in shape. Inflorescences positioned above the foliage. Inflorescences face mostly upright. Freely flowering habit; about two open inflorescences and about three developing inflorescences per lateral branch; about 46 developing and open inflorescences per plant. Inflorescences persistent.

*Fragrance.*—Slightly sour.

*Time to flower.*—Under natural season conditions, plants begin flowering in March and April and flower continuously throughout the summer.

*Post-production longevity.*—Inflorescences maintain good substance for about two to three weeks on the plant.

*Inflorescence bud.*—Height: About 1.8 cm. Diameter: About 1 cm. Shape: Roughly conical. Color: 164A.

*Inflorescence size.*—Diameter: About 7 cm. Depth (height): About 3.3 cm. Disc diameter: About 2.5 cm. Receptacle diameter: About 2.2 cm. Receptacle height: About 1 cm.

*Involucral bracts.*—Shape: Elliptical. Length, largest bracts: About 2.6 cm. Width, largest bracts: About 1 cm. Apex: Acuminate. Base: Truncate. Margin: Entire. Texture: Smooth, glabrous; papery. Orientation: Upright to horizontal to eventually reflexed. Number of involucral bracts per inflorescence: About 110 in about five whorls. Color: When opening and fully opened, upper surface: 15A; towards the apex, 172C. When opening and fully opened, lower surface: 172B.

*Disc florets.*—Arrangement: Massed in the center of the receptacle. Shape: Tubular; apex dentate, five-pointed. Length: About 1.4 cm. Diameter, apex: About 1 mm. Diameter, base: Less than 1 mm. Number of disc florets per inflorescence: About 1400. Color: Immature: 5A. Mature: Apex: 23A. Mid-section: 15B. Base: 145C.

*Phyllaries.*—Quantity per inflorescence: About 24. Length: About 1 cm. Width: About 2 mm. Shape: Linear. Apex: Acuminate. Base: Truncate, fused. Margin: Entire. Texture, upper and lower surfaces: Smooth. Color, upper and lower surfaces: Close to 137A.

*Peduncles.*—Length: About 10 cm. Diameter: About 3 mm. Strength: Strong. Aspect: Mostly upright to slightly outward. Texture: Tomentose. Color: 148C.

*Reproductive organs (present on disc florets only).*—Androecium: Quantity per disc floret: About five. Anther shape: Oblong. Anther length: About 2 mm. Anther color: 23A. Pollen amount: Moderate. Pollen color: 23A. Gynoecium: Pistil length: About 1.5 cm. Stigma shape: Bi-parted. Stigma color: 23B. Style length: About 1 cm. Style color: 23C. Ovary color: 155A.

*Seed/fruit.*—Seed and fruit production has not been observed.

Disease/pest resistance: Plants of the new *Bracteantha* have not been shown to be resistant to pathogens and pests common to *Bracteanthas.*

Temperature tolerance: Plants of the new *Bracteantha* have been observed to tolerate temperatures ranging from about 3° C. to about 35° C.

It is claimed:

1. A new and distinct *Bracteantha* plant named 'Golbra' as illustrated and described.

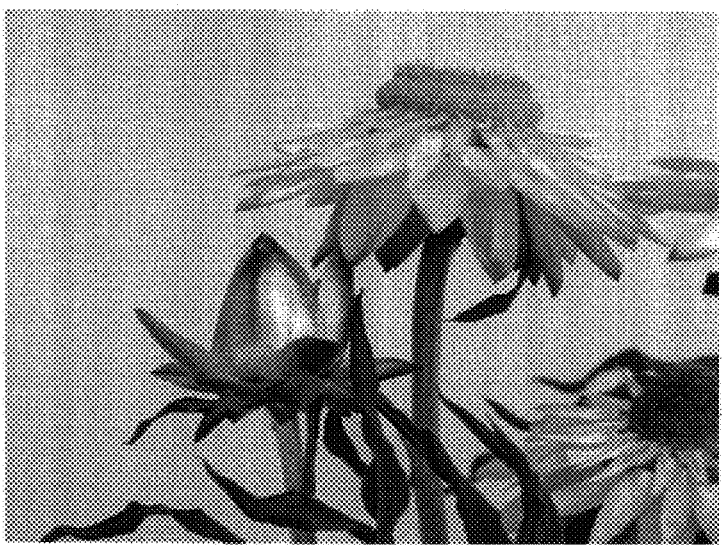
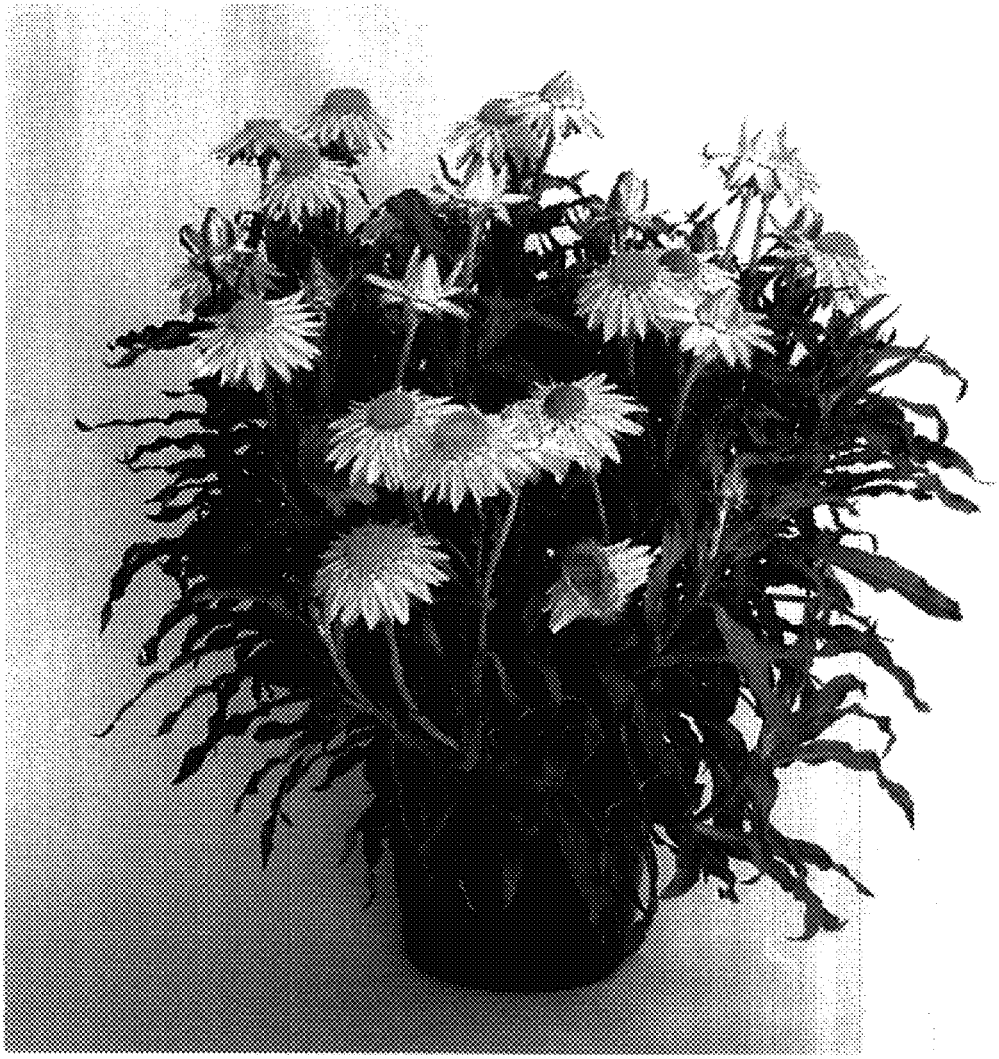

* * * * *